(12) United States Patent
Retterath et al.

(10) Patent No.: US 7,060,981 B2
(45) Date of Patent: Jun. 13, 2006

(54) SYSTEM FOR AUTOMATED DETECTION OF EMBEDDED OBJECTS

(75) Inventors: James E. Retterath, Excelsior, MN (US); Robert A. Laumeyer, Minneapolis, MN (US)

(73) Assignee: Facet Technology Corp., Eden Prairie, MN (US)

( * ) Notice: Subject to any disclaimer, the term of this patent is extended or adjusted under 35 U.S.C. 154(b) by 0 days.

(21) Appl. No.: 10/935,476

(22) Filed: Sep. 7, 2004

(65) Prior Publication Data

US 2005/0067570 A1    Mar. 31, 2005

Related U.S. Application Data

(60) Provisional application No. 60/500,594, filed on Sep. 5, 2003.

(51) Int. Cl.
*G01F 23/00* (2006.01)
(52) U.S. Cl. .................................. 250/359.1
(58) Field of Classification Search ............. 250/359.1
See application file for complete search history.

(56) References Cited

U.S. PATENT DOCUMENTS

| | | | |
|---|---|---|---|
| 3,113,448 A | 12/1963 | Hardway et al. | |
| 3,129,585 A | 4/1964 | Hamilton | |
| 3,282,115 A | 11/1966 | Taylor et al. | |
| 3,455,168 A | 7/1969 | Taylor et al. | |
| 3,487,698 A | 1/1970 | Leger, Jr. et al. | |
| 3,511,237 A | 5/1970 | Jaeger | |
| 3,557,625 A | 1/1971 | Leger, Jr. et al. | |
| 3,585,861 A | 6/1971 | Keng | |
| 3,769,834 A | 11/1973 | Fletcher et al. | |
| 4,112,738 A | 9/1978 | Turner | |
| 4,369,652 A | 1/1983 | Gundlach | |
| 4,449,406 A | 5/1984 | van Haren | |
| 4,888,718 A | 12/1989 | Furuse | |
| 5,105,825 A | 4/1992 | Dempster | |
| 5,182,764 A | 1/1993 | Peschmann et al. | |
| 5,428,657 A | 6/1995 | Papanicolopoulos et al. | |
| 5,450,750 A | 9/1995 | Abler | |
| 5,585,603 A | 12/1996 | Vogeley, Jr. | |
| 5,595,189 A | 1/1997 | Naim et al. | |
| 5,757,878 A | 5/1998 | Dobbs et al. | |
| 5,818,897 A | 10/1998 | Gordon | |
| 5,847,382 A | 12/1998 | Koch et al. | |
| 6,018,562 A | 1/2000 | Willson | |
| 6,023,497 A | 2/2000 | Takahashi et al. | |
| 6,088,423 A | 7/2000 | Krug et al. | |

(Continued)

*Primary Examiner*—David Porta
*Assistant Examiner*—Marcus Taningco
(74) *Attorney, Agent, or Firm*—Patterson, Thuente, Skaar & Christensen, P.A.

(57) ABSTRACT

A system for detecting embedded objects in a specimen that includes a transport system effecting movement of the specimen relative to an imaging zone along a transport path. The system also includes detector systems arranged to operably image the specimen in the imaging zone. Each detector system includes an emitter, detector, and a primary axis defined between the emitter and detector and that crosses the transport path. Energy from the emitter is directed along the primary axis and transmitted to a unique detector producing a succession of images as there is movement of the specimen relative to the imaging zone. The system further includes a computer system operably connected to the detector systems to receive and combine the succession of images producing a plurality of image slices that are combined as a representation of the specimen for use in detecting embedded objects in the specimen.

20 Claims, 8 Drawing Sheets

U.S. PATENT DOCUMENTS

| | | |
|---|---|---|
| 6,088,497 A | 7/2000 | Phillips et al. |
| 6,122,344 A | 9/2000 | Beevor |
| 6,151,381 A | 11/2000 | Grodzins et al. |
| 6,236,709 B1 | 5/2001 | Perry et al. |
| 6,299,524 B1 | 10/2001 | Janssen et al. |
| 6,370,223 B1 | 4/2002 | Gleason et al. |
| 6,430,255 B1 | 8/2002 | Fenkart et al. |
| 6,449,334 B1 | 9/2002 | Mazess et al. |
| 6,453,000 B1 | 9/2002 | Terashima et al. |
| 6,512,812 B1 | 1/2003 | Watanabe |
| 6,546,071 B1 | 4/2003 | Graves |
| 6,563,904 B1 | 5/2003 | Wijts et al. |
| 6,590,956 B1 | 7/2003 | Fenkart et al. |
| 6,597,759 B1* | 7/2003 | Mazess et al. ............... 378/53 |
| 6,597,761 B1 | 7/2003 | Garms, III |
| 6,600,805 B1 | 7/2003 | Hansen |
| 6,639,665 B1 | 10/2003 | Poole |
| 6,786,096 B1 | 9/2004 | Bond et al. |
| 2002/0071520 A1* | 6/2002 | Springer et al. ............. 378/57 |
| 2003/0108146 A1* | 6/2003 | Malamud .................... 378/19 |
| 2005/0015010 A1* | 1/2005 | Antich et al. ............... 600/449 |

* cited by examiner

Fig. 10

SYSTEM FOR AUTOMATED DETECTION OF EMBEDDED OBJECTS

PRIORITY CLAIM

The present application claims priority to U.S. Provisional Application No. 60/500,594, entitled "SYSTEM FOR AUTOMATED DETECTION OF EMBEDDED OBJECTS," filed Sep. 5, 2003, the disclosure of which is hereby incorporated by reference to the extent not inconsistent with the present disclosure.

FIELD OF THE INVENTION

The present invention relates generally to imaging systems and more particularly to using computed tomography to detect embedded objects.

BACKGROUND OF THE INVENTION

X-ray systems have been used for years as the primary method for bone and cartilage detection. The penetrating nature of X-rays and their variable absorption based on the density of the material make them good candidates for "seeing inside" the parts to be inspected. While X-rays seem to be an ideal solution for inspection within poultry processing facilities, the qualities of chicken breasts and their structural relationship between bone and cartilage make X-ray alone an inadequate tool for properly identifying bones and cartilage.

X-rays can simply be described as electromagnetic energy that penetrates objects and experiences absorption or transmission based on the atomic mass of the object. Unfortunately, it is very difficult for X-ray images to distinguish between a thin slice of dense material and a thicker slice of less dense material. This means that thin bones will show the same gray level on an X-ray scan as thick meat. In these situations, the shape of the foreign object must be analyzed because the grayscale level is an inadequate indicator of atomic mass.

Object shape, however, is not a clear indicator of the presence of bones or cartilage. Chicken breasts will usually have a smooth outer surface and an inner surface with irregularities such as folded meat parts and fat pieces. Unfortunately, folded meat pieces and other object characteristics on the underside of the breast cannot generally be distinguished from bones or cartilage, either in shape or in color. X-ray systems that utilize both shape and color will do a reasonable job of identifying foreign material, but the accuracy rates will not allow their use in a fully automated, unattended mode.

There have been countless movies with scenes that show law enforcement officials reviewing surveillance video where the character asks the computer operator to "enhance the image." Undoubtedly, the computer operator will be able to recover striking details from a base image that clearly did not contain this detail from the start. These scenes, unfortunately, are only possible in the movies.

The poultry industry (as well as other industries that rely on hidden object detection) has been attempting similar impossible decision making with imagery that does not contain enough information with which to make the decision. Standard, unaided X-ray imagery simply does not provide the amount of information needed to make accurate bone and cartilage detection decisions.

Even though great strides have been made in processing software to squeeze every ounce of information out of X-ray imagery, it becomes necessary in production systems to increase the quality of the information supplied to the software. Several attempts have been made to increase image quality for inspection and foreign object detection.

U.S. Pat. No. 6,023,497 discloses a single X-ray emitter with a tuned detector and U.S. Pat. No. 5,585,603 describes how to use a single emitter X-ray device for determining the weight of an object. Furthermore, U.S. Pat. No. 6,299,524 describes a single X-ray system used to determine bone fractures. Other single emitter functionality is disclosed in U.S. Pat. Nos. 6,512,812, 6,546,071 and 6,563,904.

Some increased functionality has been gained by using more than one detector for a single X-ray emitter. Specifically, U.S. Pat. No. 5,757,878 discloses a single emitter with a plurality of detectors, while U.S. Pat. No. 5,428,657 describes a single X-ray emitter system that analyzes Rayleigh and Compton scattering.

Better detection of unwanted objects has been realized by utilizing a second X-ray emitter. U.S. Pat. No. 6,600,805 describes the use of two X-ray sources, each emitting different energies, and two detectors. U.S. Pat. No. 6,370,223 builds on this concept by defining two X-ray sources, each emitting different energies, with the use of laser profilometry to determine object thickness and factor the thickness out of the X-ray imagery. U.S. Pat. Nos. 6,449,334 and 6,597,759 utilize two X-ray sources, each emitting different energies, and two detectors along with the analysis of Compton scattering.

Computed tomography (CT) systems advanced the state of the art in X-ray scanning by utilizing multiple views of a "slice" of an object. The CT systems typically include an X-ray emitter and an array of X-ray detectors connected on diametrically opposite sides of the annular disk, with the disk being mounted within a gantry support. During the scan of an object located within the opening of the disk, the disk rotates about an axis while the X-rays pass from the focal spot of the fan-shaped beam from the emitter through the inspected object to the detectors. The X-ray emitter and detector array are positioned so that X-ray paths between the focal spot and each detector all lie in the same plane (herein referred to as the "slice plane"), which is orthogonal to the travel axis of the part under inspection.

CT technology creates cross-sectional slices of an object by rotating the X-ray emitter and detector 360 degrees around the object. A cross-section is created from all of the images gathered, which are typically taken at one-degree increments for each cross section. The object under inspection is then advanced an incremental amount and the 360 degrees scan is performed again. By moving the specimen incrementally through the system and obtaining a 360 degrees slice at each increment a precise 3-D computer model of the object can be created.

U.S. Pat. No. 6,597,761 describes a single emitter CT for processing logs, while U.S. Pat. No. 5,818,897 discloses a single emitter CT with a two-dimensional array of detectors. U.S. Pat. Nos. 5,182,764, 6,430,255 and 6,590,956 all describe aspects of a single emitter CT with a single-stage X-ray pre-scan.

Several patents describe systems with CT capabilities, but with single rotational emitters replaced with multi-emitter configurations. U.S. Pat. No. 6,018,562 claims a multi-emitter configuration where the emitters and detectors are configured in L-shaped arrays. U.S. Pat. Nos. 6,088,423 and 6,236,709 disclose three-emitter systems used for baggage inspection. U.S. Pat. No. 6,453,000 claims a five-emitter system with partially overlapping X-ray beams.

These CT systems can construct somewhat accurate 3-D computer models of heterogeneous solids by stitching the contiguous slices together to form the representation of the object. If rotational and multi-emitter CT systems were fast enough, their use in meat, poultry, fish, fruit, vegetable, grain and baked goods processing facilities would allow very reliable foreign object detection with minimal false positives. For example, because poultry processing facilities must process birds at rates from 20 to 1000 birds per minute, the use of conventional CT systems for full inspection of boneless chicken pieces is not practical. Given the small size of bones and cartilage in meat products, the lack of accuracy of these CT-like systems is problematic.

There is the need for a system that can obtain the detection accuracy of CT systems, but at fast enough rates and with the required accuracy to be used for full, automated inspection of specimens in production facilities.

SUMMARY OF THE INVENTION

This invention incorporates many of the benefits of conventional CT, but in a way that allows full inspection for bones and cartilage at very high production rates. The invention modifies conventional CT scanning in three ways. First, the transport mechanism moves continuously through the image acquisition zone. Successive starting and stopping of the transport would require too much time, thus making at-speed inspection impossible. Second, the system uses stationary X-ray emitters and detectors. Using rotating devices for collecting slices would be too slow for food processing facilities. Third, the system uses multiple emitter/detector pairs that are offset within the collection zone. The emitter and detector pairs are oriented at different angles from one another, thus allowing reconstruction of the slices for all portions of the specimen.

Upon completion of the various scans for all portions of the specimen, the system creates slices from the plurality of scans, constructs the resulting 3-D model of the specimen, and analyzes the solid model for the presence of unwanted objects. The computer system controlling the imaging mechanism requires sufficient memory (either volatile or non-volatile) to hold these slices because multiple images from M detectors (where M can be as small as three and as large as 500) must be stored until the entire specimen has passed through the imaging zones for all M detectors.

The spacing between all M detectors can be the same for the entire system. In practice, the distances between successive detectors may vary throughout the mechanism. This variable spacing between detectors simply requires the software to match the appropriate image from each detector so that slices of the specimen are created from images that were captured roughly through the same plane of the inspected specimen.

The 3-D model created with this system has very distinct cues for the detection of embedded objects. The model will show the volumetric shape of the embedded object as well as the density differences between the embedded object and the surrounding material. In most implementations of this invention, analysis of the objects occurs in real time, thus allowing decisions like rejecting defective materials to be made prior to passing good parts to the next stage in a process.

This invention can be controlled by a single computer or a collection of computers. The only requirement for the system is that the analysis software can retrieve images from the multiple detectors, properly assemble them into a mathematical representation of the specimen, and analyze the mathematical model for defects or other embedded objects.

X-ray emitters are more expensive than detectors. In addition to higher cost, the emitters present power consumption and reliability concerns for production systems. Another preferred embodiment of the present invention reduces the number of X-ray emitters. The X-ray beams that are directed toward the plurality of emitters can be generated by a single X-ray emitter with beam splitters that direct the various beams toward the multitude of detectors.

While X-ray emitters are expensive, incorporating additional emitter and detector pairs can produce enhanced system reliability by allowing for operation with one or more failed emitters and/or detectors.

Slices of specimens are typically constructed with the slices oriented normal to the surface of the transport with the normal vector of the slices oriented parallel to the travel vector for the transport. Another embodiment can produce specimen slices where the slices are not parallel to the travel vector for the transport. Yet another embodiment can produce specimen slices where the slices are not oriented normal to the surface of the transport.

This invention utilizes X-ray technology to construct 3-D models, but any one of a number of energy sources could be used in place of X-ray. The only requirements for alternate energy spectra would be that the electromagnetic energy must be capable of penetrating the specimens to be inspected. Other energy sources could include, but are not limited to ultrasound, infrared, near infrared, ultraviolet, magnetic resonance, gamma rays, etc.

The system described herein utilizes collectors throughout 180 degrees of the possible 360 degrees for each scan. Another embodiment utilizes emitters and detectors that are oriented in a region as small as 100 degrees and as large as 360 degrees.

Another preferred embodiment of the invention is for the use of content analysis in specimens. For example, the mathematical model created for the specimen can be used to define the precise fat or bone content for the specimen. The weight of the specimen can be determined by identifying the volumes of all of the contained materials (by analyzing the mathematical model created for the specimen), multiplying the various volumes by the densities of those materials, and adding the weights of all of the materials.

Another preferred embodiment of the invention is for the assurance of the minimum level of an ingredient in a product. For example, the producer of diced ingredients for soup may want to ensure that all products contain at least a certain percentage of all of the necessary ingredients. The system would create a model of all of the packages either before or after they are sealed. A sorting system could then be used to reject the product that did not meet the defined quality criteria.

Another use of the invention could be for quality control and/or litigation evidence. Producers could use the defined invention to scan all products before they leave the facility. All products could be uniquely identified and their mathematical model could be archived. If a consumer claims a foreign object was contained in a sealed package, a producer could refer back to the mathematical model for the product in question to determine if the foreign object was actually contained within the package.

This invention does not require real time creation of the mathematical model and does not require real time analysis of the model. In the quality control evidence example cited in the previous paragraph, the producer may choose to simply scan all products without performing analysis.

Therefore, the analysis could be carried out only in instances where the analysis was necessary. In these situations, the computer system could be used to selectively combine stored images at a subsequent date to produce a plurality of image slices that can be combined as a representation of the specimen for use in detecting embedded objects in the specimen. Alternatively, some amount of processing may be done on the image to reduce the amount of information for storage as stored data, with the complete analysis occurring only as desired at a later time based on retrieval of the stored data.

Another embodiment of the invention allows for the progressive refinement of the model as data arrives. Non-global analysis could also be performed as scanning occurs.

The system described herein utilizes emitters that have the same angular offset between successive emitters. An alternate embodiment of the invention can utilize a plurality of emitters that have variable angular offsets. For example, when inspecting specimens where the length and width dimensions are greater than the height, it may be beneficial to have a greater concentration of emitters closer to the normal vector of the transport mechanism, with sparser concentrations of emitters at angles near the horizontal angle of the transport.

This system utilizes a conveyor or other transport system that effects movement of a specimen along a transport path through an imaging zone. A preferred embodiment of the invention could scan specimens that are moved by other means through the imaging zone. For example, the multiple emitter/detector system could be installed within a tunnel or under a bridge and could be used to scan all vehicles that passed through the imaging zone. The only requirement would be that the specimen did not change shape while traveling through the imaging zone. In an alternate embodiment of the present invention, the multiple emitter/detector system could move along a transport path while the specimen remains stationary. In a preferred embodiment, the transport system continuously effects movement of a specimen through an imaging zone during an imaging period. This allows a system to achieve high throughputs because there are no significant periods of delay. "Continuous movement" as used in connection with the present invention focuses on an overall period of movement, and not whether there is or is not motion at any given point in time. Therefore, "continuous movement" not only includes situations in which there is motion at every given point of time, but also to situations in which there may be periods of non-motion, i.e., stops of short duration, during the overall period of movement. For example, as the transport system effects movement of a specimen with respect to the transport path, there may be short periods in which motion may temporarily cease. Such stops generally are a few milliseconds or less in duration, and are typically less than one-tenth of a second. As long as such interruptions of motion are short, discrete and the acceleration and deceleration of the transport system necessary to accomplish such interruptions are relatively small, as might be accomplished, for example, by a stepper motor or servo motor controlled transport system, these interruptions should not affect the overall period of movement and thus the throughput of the entire system. It is preferably during an imaging period, any periods of non-motion comprise less than or equal to ten percent of the total imaging period, although it is intended that situations where there is motion greater than two-thirds of the time are considered to be "continuous movement" in accordance with the present invention.

The system described herein preferably utilizes a constant conveyor speed. A preferred embodiment uses precision encoders on the conveyor to determine the instantaneous speed of the object. Changing conveyor speeds can be compensated for by adjusting the timing of the capture of information for the plurality of detectors. For specimens not moved by conveyor systems, other methods can be used to track the velocity of the object through the imaging zone. Methods for tracking specimen location and velocity include, but are not limited to laser scanning, laser range finding, imaging devices, motion sensing using video, etc.

The system described herein utilizes detectors where the offsets between detectors are equal to an integer number of slices, thus allowing all detectors to be sensed in unison. A preferred embodiment eliminates the restriction of having offsets that are an integer number of slices. This embodiment will use variable timing for the sensing of the detectors to ensure that the midpoint of a slice of the specimen is in line with the detector for each capture event for that detector.

This system utilizes mathematical models to create a 3-D model of the specimen. 3-D models are preferred because they conform to the way humans can best view the specimen on a computer monitor or on a printed page. There are, however, more efficient mathematical models that can be created that do not require the construction of a 3-D viewable model of the specimen. A preferred embodiment will use other mathematical models that allow for more rapid construction of the model from the scanned imagery or will allow for more rapid analysis of the specimen being scanned. Other mathematical models can include, but are not limited to:

Implicit Surfaces
Variational Implicit Surfaces
Polygonal
Implicit
Grid Point Models
View Point Variant Point Cloud
Skinning Point Clouds
Range Image
Polygon Soup
Voxels
BSP Tree
CSG
Sweep
Mesh
Subdivision
Parametric
Scene Graph
Skeleton The above summary of the present invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENTS

The present invention can be more readily understood by reference to FIGS. 1–10 and the following description. While the present invention is not necessarily limited to such an application, the invention will be better appreciated using a discussion of example embodiments.

Figure 1:
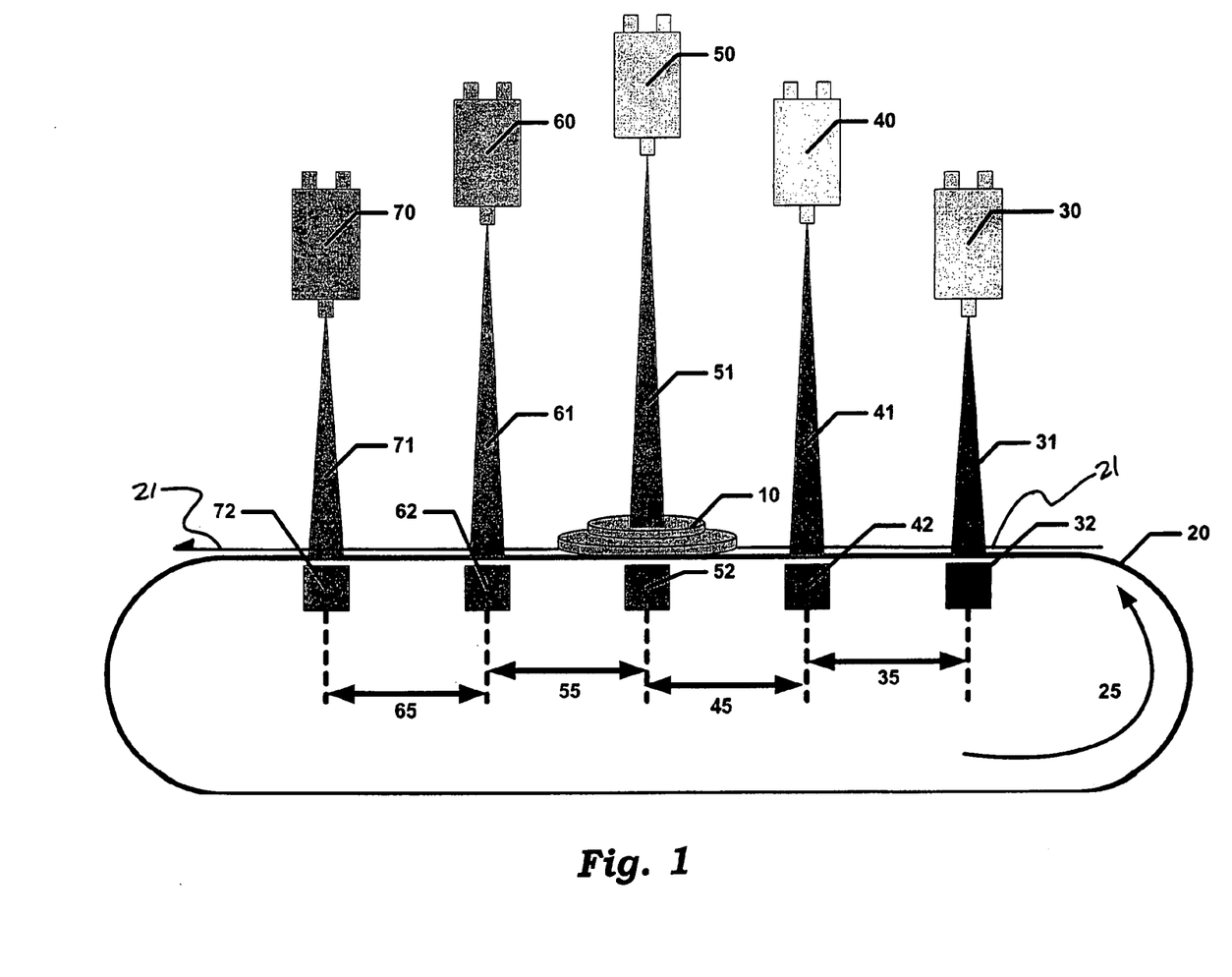
FIG. 1 depicts a side view of a five-emitter device with a conveyor that transports the specimen through the multitude of X-ray beams. This device has detectors that are parallel to the conveyor surface.

FIG. 1 depicts a side view of a preferred embodiment of the present invention. For simplicity, this figure depicts five X-ray emitter/detector pairs. However, for highly accurate object detection, it is preferred that a greater number of X-ray emitters and detectors be used. In the preferred embodiment, the specimen 10 is transported along a transport path 21 on a conveyor 20 in a direction 25 with a plurality of emitters 30, 40, 50, 60 and 70 directed at various angles toward the transport path 21 of the specimen 10. The plurality of detectors 32, 42, 52, 62 and 72 receive and record the transmitted energy from the plurality of fan-shaped X-ray beams 31, 41, 51, 61 and 71 as the specimen 10 moves through the imaging zone.

Figure 6:
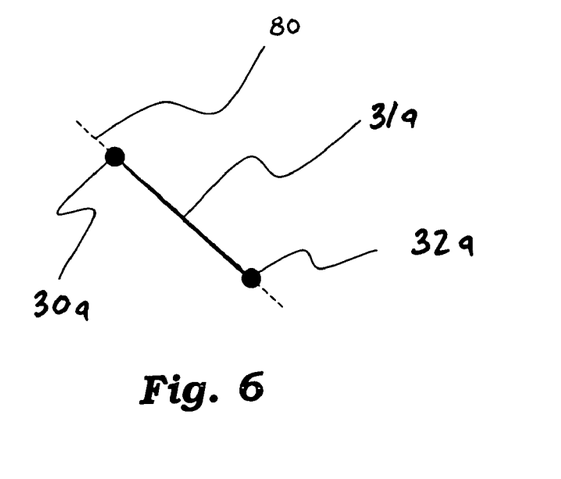
FIG. 6 depicts a side view of a point source to point detector configuration having a generally line, tube, or beam "shape" of transmitted energy.
Figure 7:
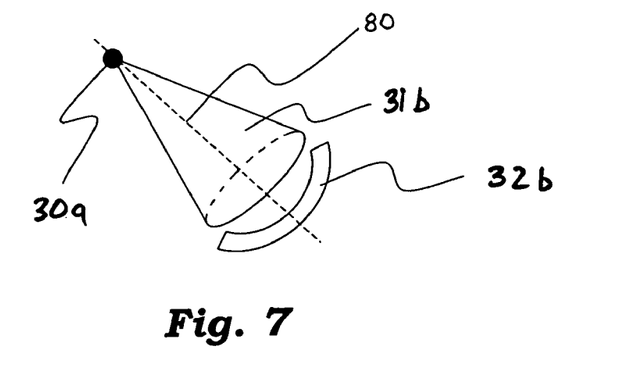
FIG. 7 depicts a side view of a point source to area detector configuration in which the X-ray beam has a generally cone two-dimensional or three-dimensional "shape" of transmitted energy.
Figure 8:
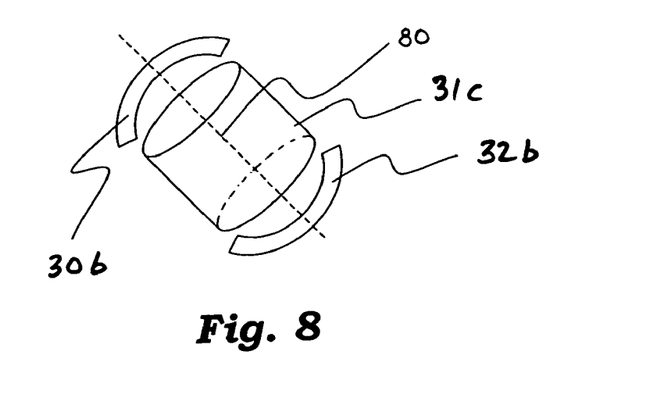
FIG. 8 depicts a side view of an area source to area detector configuration having a generally cylindrical or frusto-conical "shape" of transmitted energy.

Referring to FIGS. 6–8, the emitter/detector pairs can be configured in many different ways using point sources 30a, areas sources 30b, point detectors 32a, and area detectors 32b. Types of point sources 30a include laser diodes, X-ray diodes, solid-state discrete emitters, and collimated energy from an emitter array. Types of area sources 30b include two-dimensional emitter arrays, high-density discrete emitter devices, and beam-split energy from point sources. Types of point detectors 32a include solid-state discrete detectors, optical couplers, and photocells. Types of area detectors 30b include two-dimensional detector arrays, detector arrays with integrated scatter control, and energy-absorbent membranes. FIG. 6 depicts a point source 30a to point detector 32a configuration having a generally line, tube, or beam "shape" of transmitted energy 31a. FIG. 7 depicts point source 30a to area detector 32b configuration in which the X-ray beam has a generally cone two-dimensional or three-dimensional "shape" of transmitted energy 31b. FIG. 8 depicts an area source 30b to area detector 32b configuration having a generally cylindrical or frusto-conical "shape" of transmitted energy 31c. Therefore, although FIGS. 1–4 depict fan-shaped beams, those skilled in the art would recognize that many other types of beam shapes could be used. Regardless of which emitter/detector configuration is used, the transmitted energy "shape" of each configuration preferably centers around a primary axis 80.

Figure 2:
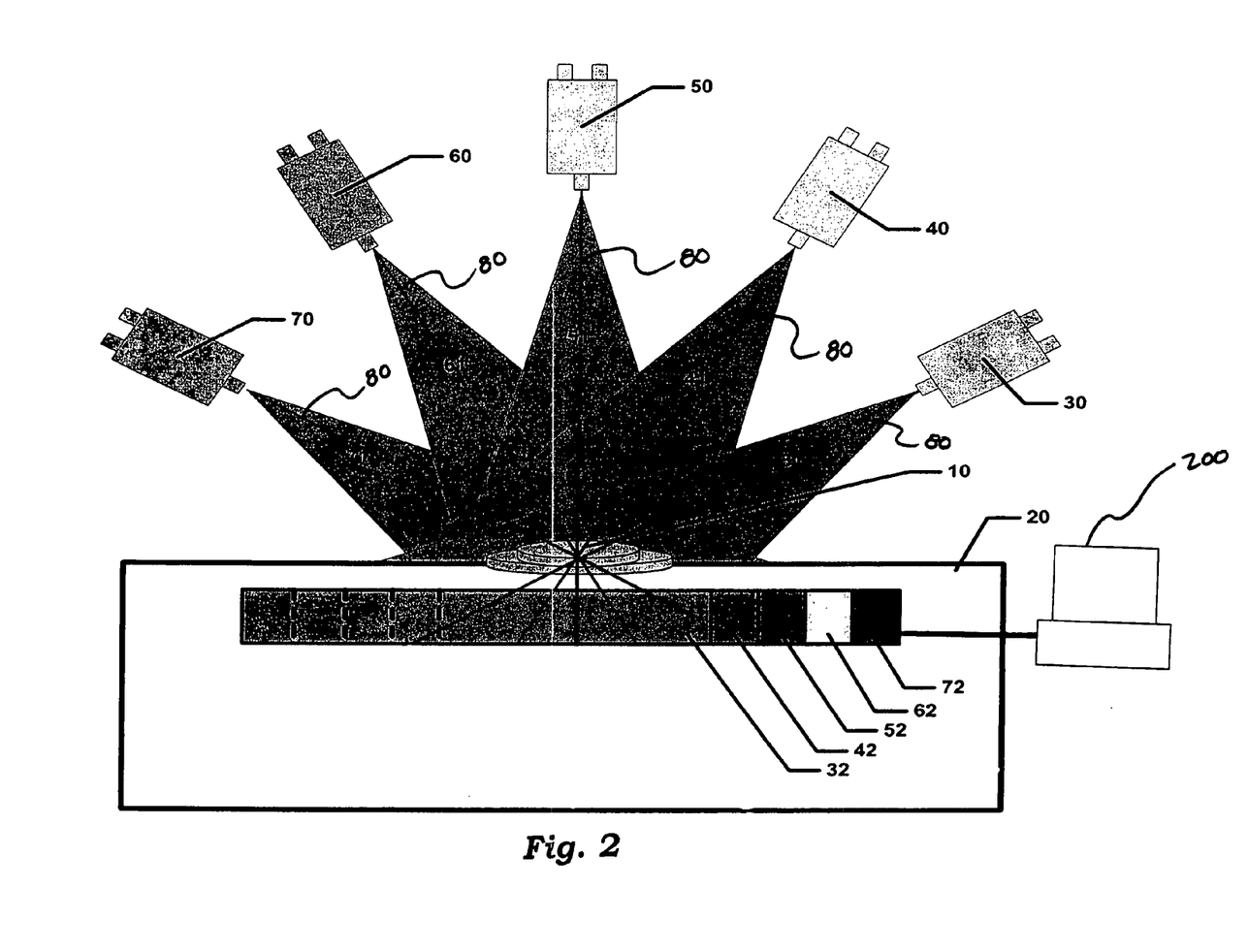
FIG. 2 depicts an end view of the system from FIG. 1. The emitters are oriented at various angles relative to the surface of the conveyor.

FIG. 2 depicts an end view of the five-emitter/detector device depicted in FIG. 1. The emitters 30, 40, 50, 60 and 70 are oriented at various angles, which allows different views through the specimen 10 and results in the ability to construct computer-resident slices 110 of the specimen 10. Because all views of a slice 110 of the specimen 10 are not taken simultaneously, a computer system 200 is preferably used to store views of a slice 110 until all of the images for a particular slice 110 have been gathered.

Figure 3:
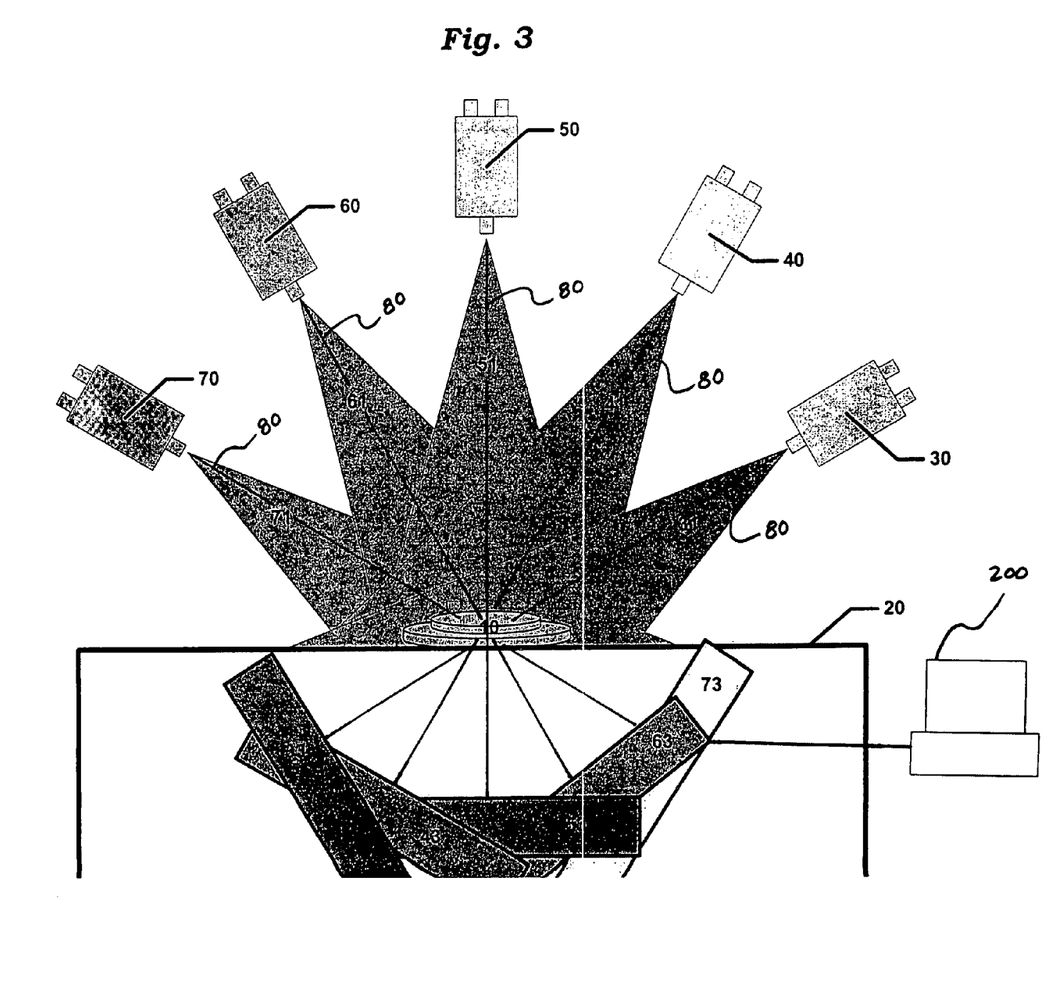
FIG. 3 depicts an end view of the multiple emitter system, but with linear detectors that are perpendicular to the axis of the fan-shaped X-ray beam.

As depicted in FIG. 2, a preferred embodiment as described above utilizes X-ray detectors 32, 42, 52, 62 and 72 that are parallel to the conveyor 20. Detectors 33, 43, 53, 63 and 73 could also be oriented parallel to each X-ray emitters 30, 40, 50, 60 and 70 (perpendicular to the primary axis of the fan-shaped beams 31, 41, 51, 61 and 71). FIG. 3 depicts an end view of a five emitter/collector device, but with linear detectors 33, 43, 53, 63 and 73 that are oriented perpendicular to the primary axes 80 of the fan-shaped beams 31, 41, 51, 61 and 71.

Figure 4:
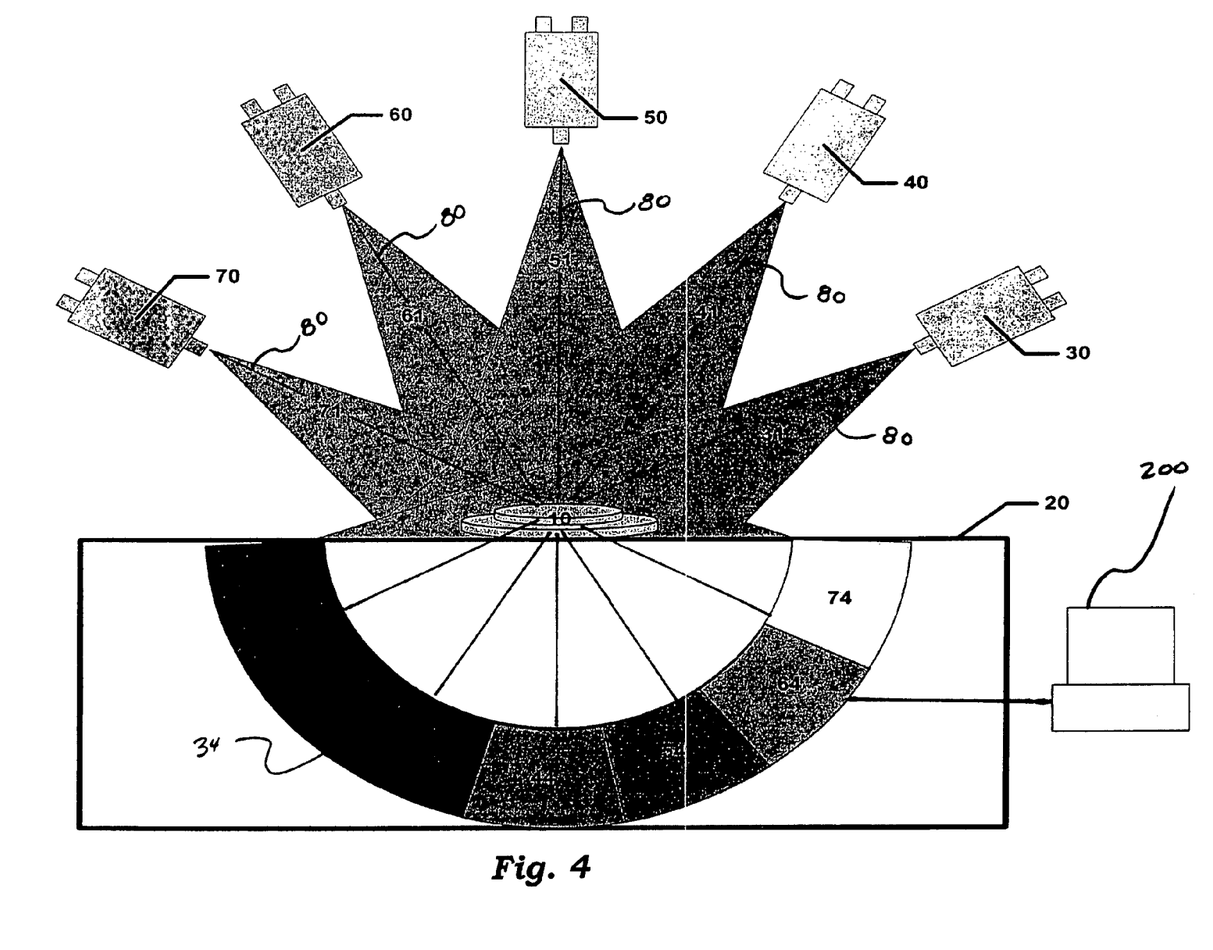
FIG. 4 depicts an end view of the multiple emitter system, but with arc-shaped detectors that are perpendicular to the axis of the fan-shaped X-ray beam.

FIG. 4 depicts an end view of a five emitter/collector device, but with arc-shaped detectors 34, 44, 54, 64 and 74 oriented perpendicular to the primary axes 80 of the fan-shaped beams 31, 41, 51, 61 and 71, where the radius of curvature and the location of the detectors 34, 44, 54, 64 and 74 is such that the detector elements are at the focal length of each of the X-ray beams 31, 41, 51, 61 and 71.

Figure 5:
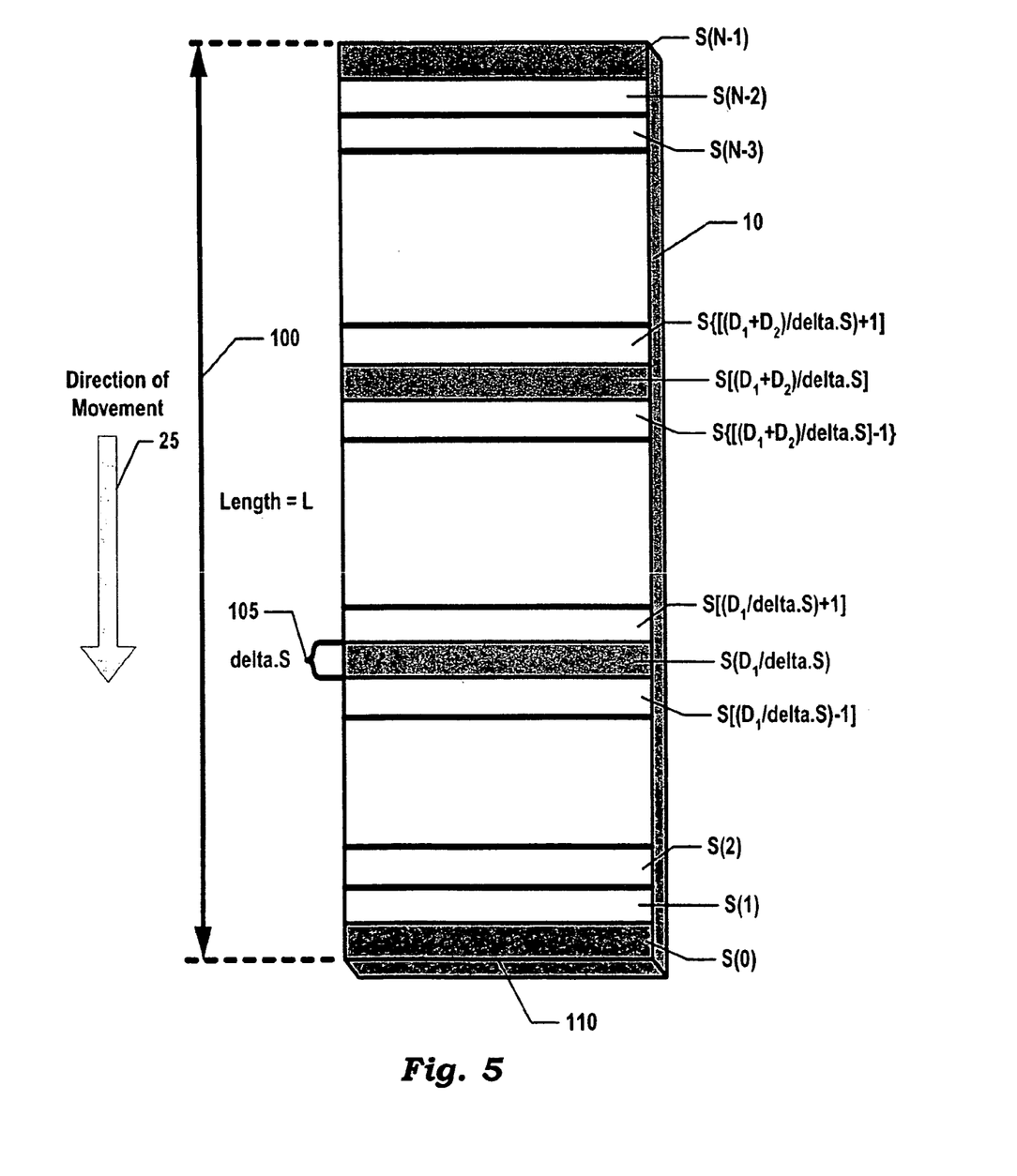
FIG. 5 depicts the top view of a simple inspected specimen along with the definitions of the slice numbering methodology for the specimen, where the slice numbering depends on the speed of the conveyor system and the distances between the detectors in the system.

FIG. 5 depicts a simple specimen 10 of length L 100 that is divided up into N discrete slices 110. The distance between midpoints of all successive slices 110 is $\Delta S$ 105. Therefore, the length 100 is expressed as:

$$L = N * \Delta S \quad \text{(Equation 1)}$$

The distances 35, 45, 55 and 65 between the M X-ray emitters 30, 40, 50, 60 and 70 are expressed as:

$$D_i, i = 0 \text{ to } M-1 \quad \text{(Equation 2)}$$

Image slices 110 are mathematic combinations of images collected from all M detectors and are expressed as:

$$S(n) = I(0,n)$$

$$\Sigma I(1, n + D_1/\Delta S)$$

$$\Sigma I(2, n + (D_1 + D_2)/\Delta S)$$

$$\ldots$$

$$\Sigma I(M-1, n + \Sigma_{j=1 \text{ to } M-1} D_j/\Delta S) \quad \text{(Equation 3)}$$

Where: n varies from 0 to N−1
I(k, m) is the image number where:
k=the detector number
m=the sample number
Ξ is a mathematical operation performed on image pixels The mathematical representation of the specimen 10 is then expressed as:

$$\text{Model} = \Sigma_{j=1 \text{ to } N-1} S(j),\quad \text{(Equation 4)}$$

Where: N=number of slices in the specimen
S(j) is the mathematical model of slice j Equation 4 signifies a summation of slices, wherein the summation is a mathematical operation that fuses 3-D volumetric slices together into a single, 3-D model. This summation function will actually be an independent mathematical operator based on the particular mathematical model being utilized for analysis.

In the preferred embodiment where M emitters 30, 40, 50, 60 and 70 have equal angular offsets from one another, the angles of the M emitters 30, 40, 50, 60 and 70 are expressed as:

$$\theta_k = k*[180/(M+1)] \quad \text{(Equation 5)}$$

Where: k varies from 1 through M
θ is expressed as degrees from horizontal

The mathematical model described above is for a system wherein every slice is the same lateral thickness ΔS. One embodiment of the invention allows every slice to be a different thickness, $\Delta S_i$. One skilled in the art could modify the aforementioned equations to utilize varying slice thicknesses $\Delta S_i$.

Figure 9:
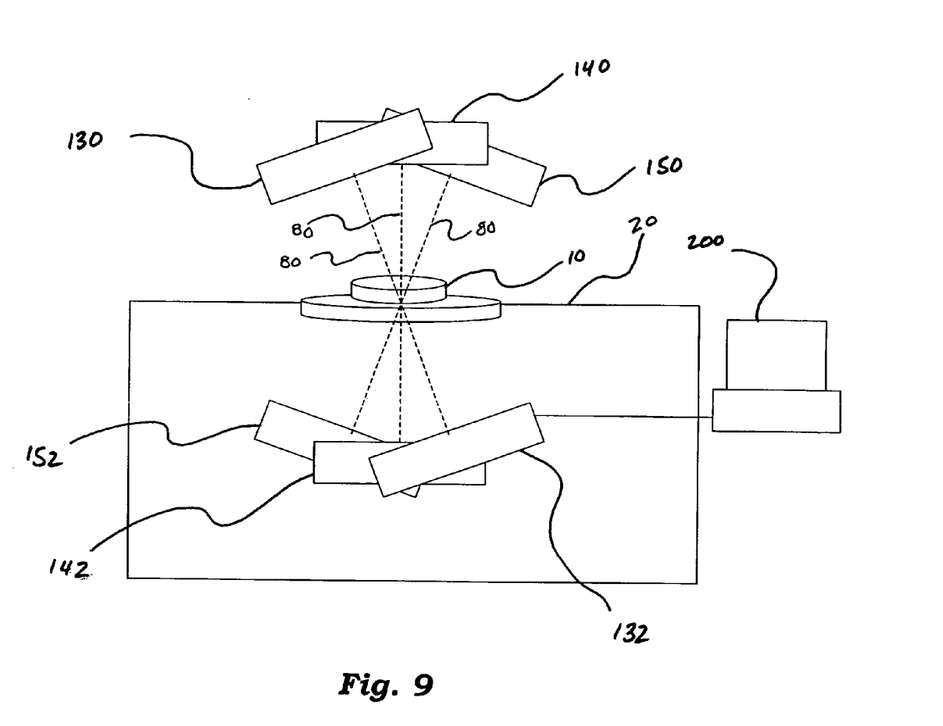
FIG. 9 depicts an end view of a system having emitter and detector arrays with a conveyor that transports the specimen through the multitude of X-ray beams.

FIG. 9 depicts an end view of another embodiment of the present invention. The system depicted in FIG. 9 includes three detectors systems each comprising an emitter array (depicted as emitter arrays 130, 140, 150) and a detector array (depicted as detector arrays 132, 142, 152) that are oriented generally parallel to each other and generally perpendicular to a primary axis 80 extending between the emitter array and detector array. Each detector system is preferably defined in a distinct plane (a "slice plane") oriented generally orthogonal to the transport path 21. While it is preferred that the spacing between the distinct slice planes is equal, it is not necessary that the spacing be equal. When the primary axes 80 are projected along the transport path 21 onto a common plane defined perpendicular to the transport path 21, the primary axes 80 for each of the detector systems intersect one another.

Figure 10:
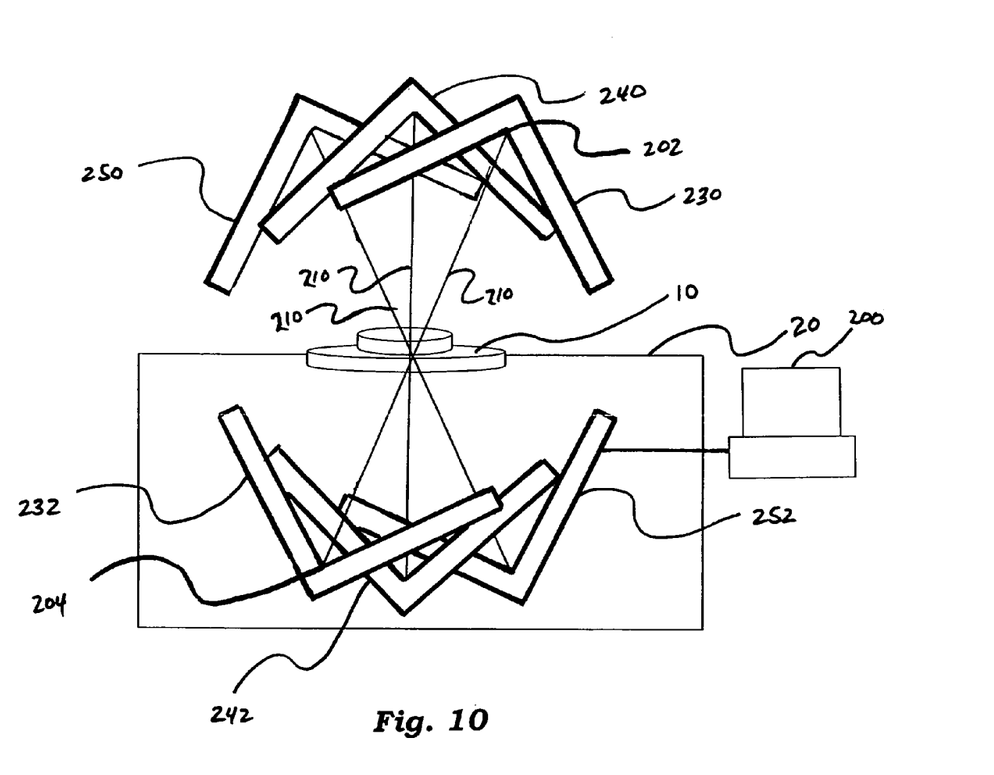
FIG. 10 depicts an end view of a system having L-shaped emitter and detector arrays with a conveyor that transports the specimen through the multitude of X-ray beams.

FIG. 10 depicts an end view of further embodiment of the present invention. The system depicted in FIG. 10 comprises L-shaped emitter arrays 230, 240, 250 and detector arrays 232, 242, 252 in which an array of emitters is used in place of a single emitter and an array of detectors is used in place of a single detector. FIG. 10 depicts a system comprising three emitter array/detector array pairs, each emitter array/detector array pair comprising an L-shaped emitter array (depicted as 230, 240, 250) having a first apex 202 and a generally L-shaped detector array (depicted as 232, 242, 252) having an second apex 204 generally facing the first apex 202, the emitter arrays 230, 240, 250 and detector arrays 232, 242, 252 being positioned such that the transport path 21 is intermediate the first apex 202 and second apex 204 and a line 210 between the first apex 202 and the second apex 204 defines an angular orientation of that detector system with respect to the transport path 21. The emitter array/detector array pairs are preferably each defined in distinct slice planes oriented generally orthogonal to the transport path 21. While it is preferred that the spacing between the distinct planes is equal, it is not necessary that the spacing be equal. It is preferred that successive detector systems have different angular orientations with respect to the transport path 21.

The present invention may be embodied in other specific forms without departing from the essential attributes thereof, therefore, the illustrated embodiments should be considered in all respects as illustrative and not restrictive.

What is claimed:

1. A system for detecting embedded objects in a plurality of specimens comprising:
   a transport system that uses a conveyer apparatus to provide continuous movement of the plurality of specimens relative to an imaging zone along a transport path;
   at least three detector systems arranged to operably image each specimen in the imaging zone, each detector system comprising an emitter and detector that are stationary with respect to the transport path with a primary axis defined between the emitter and the detector that crosses the transport path and along which an energy from the emitter is directed at and transmitted to a unique detector to produce a succession of images of at least a portion of the specimen as the specimen moves relative to the imaging zone, wherein the primary axis for each of the at least three detector systems intersect one another when projected along the transport path onto a common plane defined perpendicular to the transport path; and
   at least one computer system operably connected to the at least three detector systems that receive the succession of images from the detectors and combines the images to produce a plurality of image slices that are combined as a representation of each specimen for use in detecting embedded objects in the plurality of specimens,
   wherein each emitter is oriented at a different angle with respect to the transport path and each emitter is separated from adjacent emitters by an angular spacing.

2. The system of claim 1, wherein the emitters are selected from the group consisting of:
   point source;
   area source; or
   any combination thereof.

3. The system of claim 1, wherein the detectors are selected from the group consisting of:
   point detector;
   area detector; or
   any combination thereof.

4. The system of claim 1, wherein the angular spacing between the emitters is equal.

5. The system of claim 1, wherein the angular spacing between emitters is not equal.

6. The system of claim 1, wherein the detectors are generally perpendicular to the primary axis.

7. The system of claim 1, wherein the detectors are generally parallel to the transport path.

8. The system of claim 1, wherein each emitter emits X-rays.

9. The system of claim 1, wherein each emitter emits electromagnetic energy selected from the group of:
   an ultrasound energy source;
   an infrared energy source;
   a near infrared energy source;
   an ultraviolet energy source;
   a magnetic resonance source;
   gamma ray energy source; or
   any combination thereof.

10. The system of claim 1, wherein the representation comprises a three-dimensional model of each of the plurality of specimens.

11. The system of claim 10, wherein the three-dimensional model of the specimen comprises a volumetric shape of an embedded object if an embedded object is present in the specimen.

12. The system of claim 11, wherein the three-dimensional model of the specimen further comprises density differences detected by the system between an embedded object and the portion of the specimen surrounding the embedded object if an embedded object is present in the specimen.

13. A system for detecting embedded objects in a plurality of specimens comprising:
 a transport system that uses a conveyer apparatus to provide continuous movement of the plurality of specimens relative to an imaging zone along a transport path;
 at least three detector systems arranged to operably image each specimen in the imaging zone, each detector system comprising an emitter and detector that are stationary with respect to the transport path with a primary axis defined between the emitter and the detector that crosses the transport path and along which an energy from the emitter is directed at and transmitted to a unique detector to produce a succession of images of at least a portion of the specimen as the specimen moves relative to the imaging zone, wherein the primary axis for each of the at least three detector systems intersect one another when projected along the transport path onto a common plane defined perpendicular to the transport path; and
 at least one computer system operably connected to the at least three detector systems that receive the succession of images from the detectors and combines the images to produce a plurality of image slices that are combined as a representation of each specimen for use in detecting embedded objects in the plurality of specimens,
 wherein the detectors are arc-shaped and are generally perpendicular to the primary axis.

14. A system for detecting embedded objects in a plurality of specimens comprising:
 a transport system that uses a conveyer apparatus to provide continuous movement of the plurality of specimens relative to an imaging zone along a transport path;
 at least three detector systems arranged to operably image each specimen in the imaging zone, each detector system comprising an emitter and detector that are stationary with respect to the transport path with a primary axis defined between the emitter and the detector that crosses the transport path and along which an energy from the emitter is directed at and transmitted to a unique detector to produce a succession of images of at least a portion of the specimen as the specimen moves relative to the imaging zone, wherein the primary axis for each of the at least three detector systems intersect one another when projected along the transport path onto a common plane defined perpendicular to the transport path; and
 at least one computer system operably connected to the at least three detector systems that receive the succession of images from the detectors and combines the images to produce a plurality of image slices that are combined as a representation of each specimen for use in detecting embedded objects in the plurality of specimens,
 wherein the image slices are not orthogonal to the transport path.

15. A method for detecting embedded objects in a specimen comprising the steps of:
 effecting movement of a specimen relative to an imaging zone along a transport path;
 providing at least three detector systems comprising a stationary emitter and a stationary detector with a primary axis defined between the emitter and detector that crosses the transport path and along which an energy from the emitter is transmitted to a unique detector to produce a succession of images of at least a portion of the specimen as there is movement of the specimen relative to the imaging zone, wherein the primary axis for each of the at least three detector systems intersect one another when projected along the transport path onto a common plane defined perpendicular to the transport path; and
 using a computer system operably connected to the at least three detector systems to receive the succession of images from the detectors and combine the images to produce a plurality of image slices that are combined as a representation of the specimen for use in detecting embedded objects in the specimen,
 wherein there is continuous movement of the specimen through the imaging zone at a variable speed and the variable speed is compensated for by adjusting a timing of receiving images from the detectors.

16. The method of claim 15, wherein the variable speed of the specimen as it moves through the imaging zone is measured by use of a device selected from the set consisting of: encoder devices, laser devices, video devices, or any combination thereof.

17. A method for detecting embedded objects in a specimen comprising the steps of:
 effecting movement of a specimen relative to an imaging zone along a transport path;
 providing at least three detector systems comprising a stationary emitter and a stationary detector with a primary axis defined between the emitter and detector that crosses the transport path and along which an energy from the emitter is transmitted to a unique detector to produce a succession of images of at least a portion of the specimen as there is movement of the specimen relative to the imaging zone, wherein the primary axis for each of the at least three detector systems intersect one another when projected along the transport path onto a common plane defined perpendicular to the transport path; and
 using a computer system operably connected to the at least three detector systems to receive the succession of images from the detectors and combine the images to produce a plurality of image slices that are combined as a representation of the specimen for use in detecting embedded objects in the specimen,
 wherein there is continuous movement of the specimen through the imaging zone for an imaging period, the imaging period comprising periods of motion and periods without motion, the periods of without motion being less than or equal to one-third of the imaging period.

18. The method of claim 17, wherein the periods without motion are less than or equal to ten percent of the imaging period.

19. The method of claim 17, wherein each period without is less than one-tenth of a second.

20. A system for detecting embedded objects in a specimen comprising:

a transport system that effects movement of the specimen relative to an imaging zone along a transport path;

at least three detector systems, each detector system defined in a distinct plane oriented generally orthogonal to the transport path and arranged to operably image the specimen in the imaging zone, each detector system comprising a generally L-shaped emitter array having a first apex and a generally L-shaped detector array having an second apex generally facing the first apex, the emitter array and detector array positioned such that the transport path is intermediate the first apex and second apex and a line between the first apex and the second apex defines an angular orientation of that detector system with respect to the transport path, successive detector systems having different angular orientations with respect to the transport path;

energy transmitted between emitter arrays and detector arrays crossing the transport path to produce a succession of images of at least a portion of the specimen as there is movement of the specimen relative to the imaging zone; and at least one computer system operably connected to the at least three detector systems that receives the succession of images from the detectors and combines the images to produce a plurality of image slices that are combined as a representation of the specimen for use in detecting embedded objects in the specimen.

* * * * *